United States Patent [19]

Bennett

[11] 3,976,579

[45] Aug. 24, 1976

[54] NOVEL ASSEMBLY

[75] Inventor: Michael C. Bennett, Summit, N.J.

[73] Assignee: Becton, Dickinson and Company, East Rutherford, N.J.

[22] Filed: July 10, 1975

[21] Appl. No.: 594,712

[52] U.S. Cl. .......................... 210/516; 23/258.5 R; 210/DIG. 23; 233/26
[51] Int. Cl.² ........................................ B01D 21/26
[58] Field of Search ............ 23/230 B, 258.5, 259, 23/292; 128/2 F, 214 R, 218 M, 272.1, DIG. 5, DIG. 28, 272, 272.3; 210/83, 84, 514–518, DIG. 23, DIG. 24; 233/1 A, 1 R, 26; 206/219, 221, 222; 215/DIG. 8

[56] References Cited
UNITED STATES PATENTS

| 2,812,231 | 11/1957 | Zar | 210/DIG. 23 |
| 3,139,121 | 6/1964 | Ballin | 215/DIG. 8 |
| 3,780,935 | 12/1973 | Lukacs et al. | 210/83 X |
| 3,852,194 | 12/1974 | Zine, Jr. | 210/83 |
| 3,920,549 | 11/1975 | Gigliello et al. | 210/DIG. 23 |
| 3,920,557 | 11/1975 | Atres | 210/DIG. 23 |

Primary Examiner—Charles N. Hart
Assistant Examiner—Robert G. Mukai
Attorney, Agent, or Firm—Kane, Dalsimer, Kane, Sullivan and Kurucz

[57] ABSTRACT

Disclosure is made of an improved assembly for the collection, separation and isolation of serum or plasma from blood without subjecting the desired serum or plasma to contamination by exposure to the atmosphere and which utilizes a thixotropic barrier material to effect the isolation. A representative embodiment of the improved assembly comprises an air-evacuated glass collection container, a self-sealing, airtight elastomeric closure for the container which is penetrable by a blood bearing cannula and a thixotrope having a specific gravity of from about 1.03 to about 1.09 disposed in a specially constructed reservoir positioned adjacent to the closure member and within the air-evacuated collection container.

1 Claim, 4 Drawing Figures

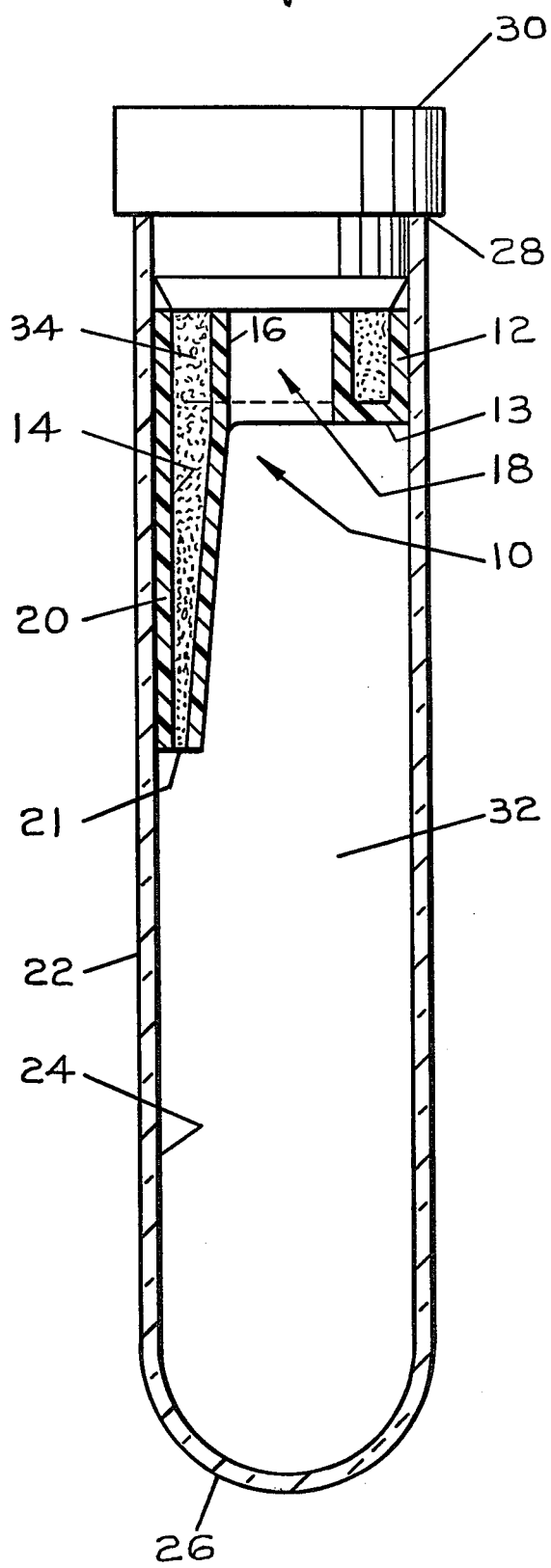
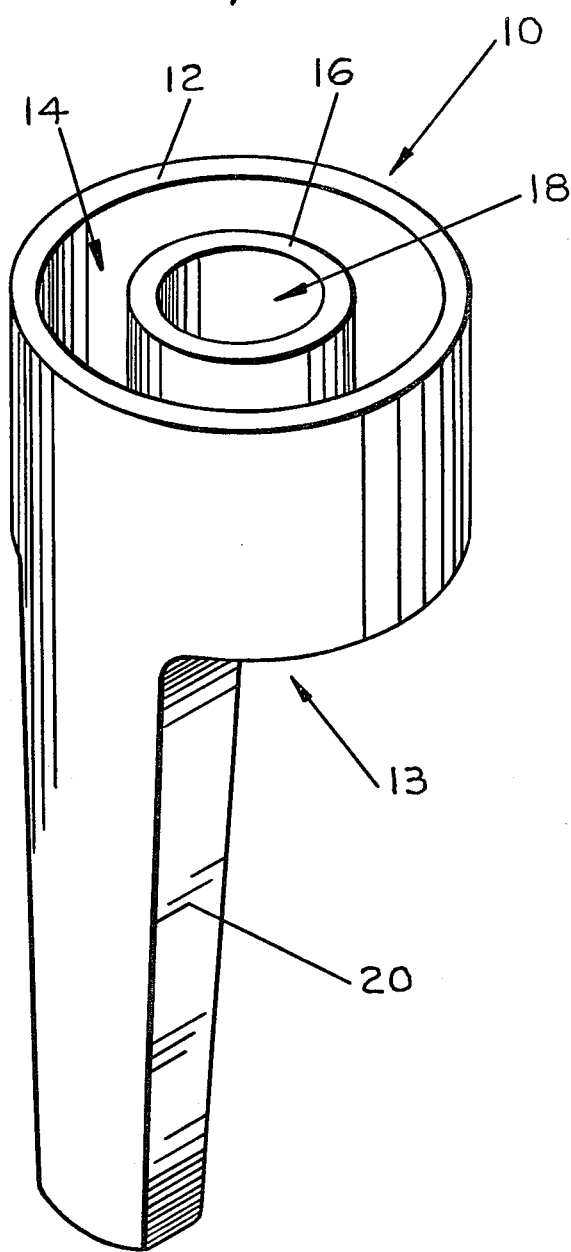

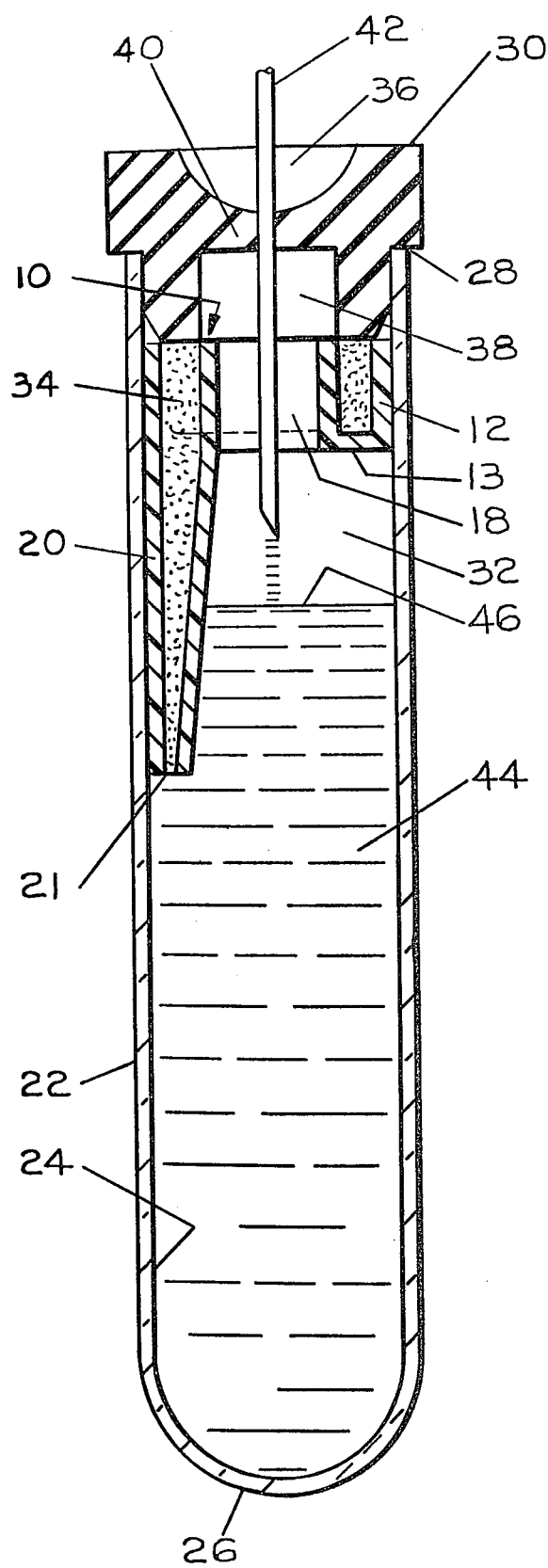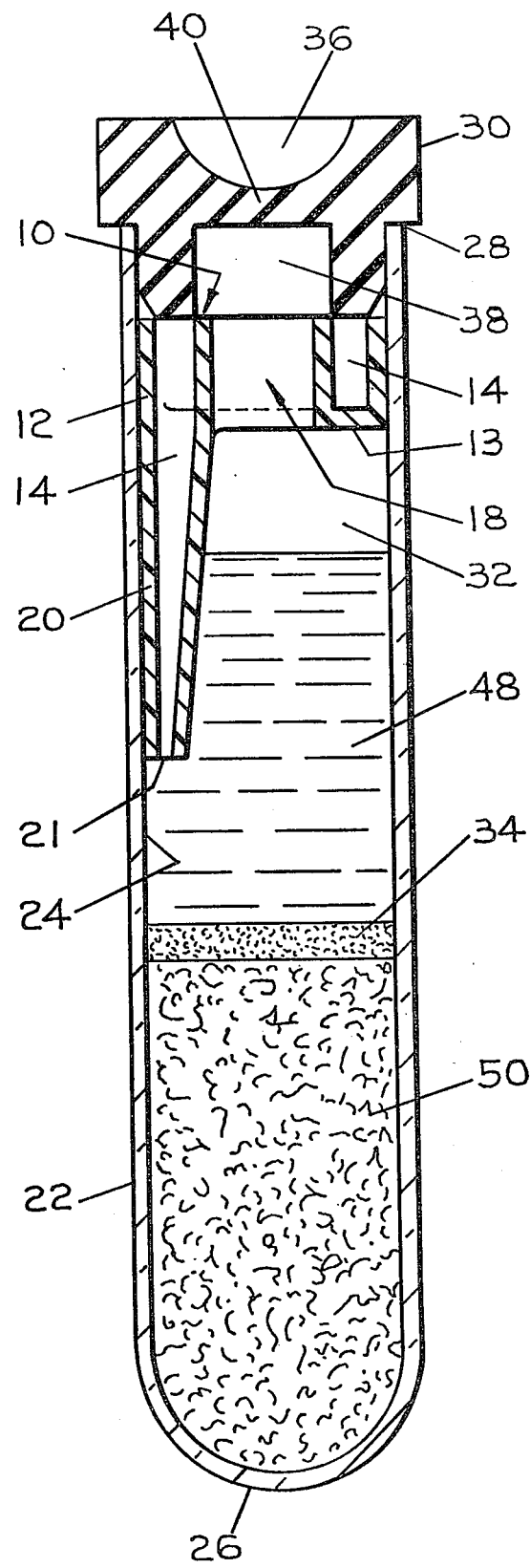

NOVEL ASSEMBLY

BACKGROUND OF THE INVENTION

1. Field of the Invention

The invention concerns the centrifugal separation of blood into its component parts of serum or plasma and cellular material and more specifically concerns an assembly for the collection, separation and isolation of serum or plasma from blood by the application of centrifugal force.

2. Brief Description of the Prior Art

Prior hereto apparatus for isolating blood serum from whole blood by centrifugation of the blood in the presence of a thixotropic sealant was disclosed in U.S. Pat. No. 3,780,935. U.S. Pat. No. 3,852,194 discloses an assembly for isolating blood serum from whole blood by centrifugation to emplace a thixotropic sealant barrier. In the latter disclosure, the assembly comprises an air-evacuated blood collection chamber within which there is loosely disposed a thixotrope. In such and assembly there is a tendency for the loose thixotrope to coat the inner walls of the blood collection container. This coating prevents the subsequently collected blood from contacting the glass walls. Contact between the collected blood and the glass is desirable to facilitate the rapid clotting of the blood, prior to centrifugation.

The assembly of my invention is an improvement over the prior art. For example, the assembly of my invention permits one to use a thixotrope sealant to isolate the serum or plasma from the substantially cellular portion of the blood rapidly and without prolonging clot formation of the collected whole blood. The assembly of my invention is also economical to construct and does not require extensive training to operate.

SUMMARY OF THE INVENTION

The invention comprises an assembly for the collection, separation and isolation of serum or plasma from the substantially cellular components of blood, which comprises;

a. means for collecting and enclosing blood without exposing said blood to contamination by airborne contaminants;

b. a reservoir adapted to hold a thixotrope sealant, disposed completely within said means in a position above that point within said means which becomes occupied by the collected and enclosed blood;

c. a thixotrope sealant disposed in said reservoir, said thixotrope having a specific gravity within the range of from about 1.03 to about 1.09; and d. means of releasing said thixotrope at a point beneath the surface of the enclosed blood, in response to centrifugal force applied to the blood filled assembly.

The assembly of the invention is useful to protect the desired serum or plasma from contamination by airborne contaminants such as, for example, lead compounds, airborne bacteria, nitrogen oxides and the like which would adversely affect certain diagnostic testing.

BRIEF DESCRIPTION OF THE DRAWINGS

FIG. 1 is an isometric view of a thixotrope reservoir component of an embodiment assembly of the invention.

FIG. 2 is a cross-sectional side elevation of an embodiment assembly of the invention.

FIG. 3 is a cross-sectional side elevation of the embodiment of FIG. 2 during the filling of the assembly with blood.

FIG. 4 is a cross-sectional side elevation as in FIG. 3 but following separation and isolation of the serum or plasma from the blood.

DETAILED DESCRIPTION OF THE INVENTION

A complete understanding of the invention may be conveniently obtained by referring to the illustrative embodiments shown in the accompanying drawings of FIGS. 1–4, inclusive.

FIG. 1 is an isometric view of a thixotrope reservoir component 10 of an embodiment assembly of the invention. The reservoir 10 consists of a tubular body 12 having an open upper end and a closed lower end 13 (not seen in FIG. 1). The tubular body 12 together with its open and closed ends defines a space 14 for holding a thixotrope sealant barrier material (not shown in FIG. 1). Traversing space 14 and the lower closed end 13 of tubular body 12 is a conduit 16 which provides an open passageway 18 through body 12, end 13 and space 14. The lower end 13 has an integral nozzle 20 which opens into reservoir 14 to provide communication between reservoir 14 and the outside of body 12. Nozzle 20 comprises a means of releasing thixotrope from space 14 as will be discussed more fully hereinafter.

Referring now to FIG. 2, a cross-sectional side elevation of an embodiment assembly of the invention using the reservoir 10, there is seen a tubular glass container 22 having a closed end 26 and an open end 28. The tubular glass container 22 with its open and closed ends defines a blood collection chamber 32. Hermetically sealing end 28 is a self-sealing, airtight, cannula-penetrable elastomeric closure 30. Although only one sealed opening is present in the embodiment of FIG. 2, the end 26 may be open but sealed with another hermetic closure 30. Mounted just beneath closure 30 is the thixotrope reservoir 10 which is attached or secured to the inner walls 24 of tubular glass container 22. Attachment may be obtained by adhesive or by a tight interference fit between body 12 and the inner walls 24 of the tubular glass container 22. In a preferred embodiment, the body 12 is attached to the underside of closure member 30 so that it is removable upon removal of member 30 thus providing greater access to chamber 32 when desired. Mounted in this position with nozzle 20 adjacent to the inner walls 24 of container 22, passage 18 provides communication between closure member 30 and the blood collection chamber 32. Blood collection chamber 32 is at least partially air-evacuated to provide at least a partial vacuum therein. As shown in FIG. 2, space 14 of reservoir 10 is filled with a thixotropic sealant 34 barrier material which extends into nozzle 20. Aperture 21 at the lower end of nozzle 20 has a width which is insufficient to permit the passage of thixotrope 34 under the force of 1 gravity. However, the width of aperture 21 is sufficient to permit the passage of thixotrope 34 under centrifugal force. The exact diameter or size of aperture 21 will vary depending upon the degree of thixotropy in thixotrope 34. In general, the greater the degree of thixotropy in thixotrope 34, the larger may be the diameter or size of aperture 21. Those skilled in the art will appreciate that the width of aperture 21 is dependent upon the degree of thixotropy of thixotrope 34 for proper operation and will know how to select a proper size employing trial and error techniques.

Thixotropic sealant 34 barrier materials which may be employed in establishing a partition or barrier between separate blood phases are generally well-known in the art. Generally, they are gel-like materials which are thixotropic and are inert to reaction with blood, blood components or reagents commonly employed in diagnostic procedures with blood specimens. Preferably, the thixotrope 34 is a hydrophobic material. The thixotropic sealant 34 barrier material will have a specific gravity within the range of from about 1.03 to about 1.09, preferably 1.06. Illustrative of thixotropic sealant 34 barrier materials which may be employed in the assembly of the invention are blends of silicone oils with inert materials such as silicon dioxide. Specific thixotrope 34 materials which may be employed in the separation of blood are well-known to those skilled in the art; see for example the disclosures of U.S. Pat. Nos. 3,780,935 and 3,852,194 which list and teach the preparation of thixotropic sealant 34 materials for separation of blood into its component liquid and solid phases.

The operation of the assembly of FIG. 2 may be readily appreciated by referring now to FIG. 3. FIG. 3 is a cross-sectional side elevation of the embodiment as seen in FIG. 2 but during the filling of the blood collection chamber 32 with blood 44. Generally, the assembly of FIG. 3 is initially air-evacuated so that there is a partial vacuum within blood collection chamber 32. As shown in FIG. 3, closure member 30 has a recess 36 in the upper portion thereof and a recess 38 in the lower portion thereof to provide a thin, cannula-penetrable zone 40. As shown in FIG. 3, a blood bearing cannula 42 has been inserted through zone 40 of closure 30 and on through passageway 18 traversing the thixotrope reservoir 10. Blood 44 has been conveyed by cannula 42 into the blood collection chamber 32 to nearly fill chamber 32. Cannula 42 is connected to a conventional closed blood transfer apparatus (not shown) such as is conventionally employed to transfer blood from a source to a recipient vessel. The reservoir 10 is positioned above the collected and enclosed blood 44. It will be noted from FIG. 3 that the nozzle 20 extends below the fill line 46 of blood 44 to serve as a means for releasing thixotrope 34 at a point beneath the surface of the enclosed blood 44 as will be disclosed hereinafter. Upon completion of collecting and enclosing blood 44 in chamber 32, cannula 42 is withdrawn from the assembly. The self-sealing, elastomeric closure 30 seals the opening made by cannula 42 during penetration of thin zone 40. Thus, the assembly of FIG. 2 (or 3) serves as a means for collecting and enclosing blood 44 without sxposing blood 44 to airborne contaminants. Following the filling of the assembly of FIG. 2 with blood 44, the assembly is preferably allowed to stand for about 30 minutes so that a clot will be formed in the whole blood. Clot formation is relatively rapid since the collected blood 44 is in contact with the inner walls 24 of glass container 22. This contact promotes clotting as is well known. Alternatively, if plasma is desired, chamber 32 may be precharged with an anti-coagulant so that entering blood 44 will be treated with an anticoagulant. In the next step for operating the assembly of FIG. 2, the blood filled assembly is centrifuged to effect a separation of blood serum or plasma from the substantially cellular portion of the blood, employing conventional technique.

Referring now to FIG. 4, a cross-sectional side elevation as seen in FIG. 3 but following centrifugal separation and isolation of serum from blood 44 it is seen that under centrifugal force, the blood 44 separated into light serum 48 and heavy substantially cellular portion 50. Concurrent with separation of the blood 44 into its component phases, sealant 34 previously disposed in space 10 was carried down under centrifugal force through aperture 21 and into blood 44 at a point beneath the surface of blood 44. Having a specific gravity which is intermediate between that of serum 48 (circa less than about 1.03) and cellular portion 50 (circa more than about 1.09) thixotrope sealant 34 establishes a sealed barrier at the interface between serum 48 and cellular portion 50. Under the force of one gravity, thixotropic sealant 34 forms a relatively rigid, gel-like barrier. Following separation and isolation of the serum or plasma 48 from the blood 44 as described above, closure 30 may be removed to gain access to the desired serum or plasma 48 or it may be withdrawn through a cannula. It will be noted that up until this time the desired blood serum or plasma 48 has not been exposed to the atmosphere and airborne contaminants nor has there been an opportunity for loss of dissolved blood gases into the atmosphere. If desired, protection of the desired serum or plasma 48 from contaminants or gas loss may be continued by withdrawing the desired serum or plasma 48 through a cannula inserted through thin zone 40 of closure 30.

What is claimed:
1. An assembly for the collection, separation and isolation of serum or plasma from blood, which comprises;
   a. a tubular container having an open end and a closed end and which together with its ends defines a blood collection chamber;
   b. a self-sealing, cannula-penetrable, elastomeric closure member hermetically sealing said open end;
   c. a thixotrope reservoir secured to an inner wall of said container adjacent to said closure member, which comprises;
      i. a tubular body having a closed lower end which defines a thixotrope holding space,
      ii. a conduit passing through the center of said reservoir and providing communication between the adjacent closure member and said blood collection chamber; and
      iii. an open nozzle extending downwardly from said reservoir along an inner wall of said container and providing communication between said holding space and the blood collection chamber, said nozzle being of a dimension which is insufficient to permit the passage of a thixotrope under the force of one gravity but sufficient to permit the passage of said thixotrope under centrifugal force; and
   d. a thixotropic sealant disposed in said holding space, said thixotrope being inert with respect to the blood and having a specific gravity within the range of from about 1.03 to about 1.09;
said assembly being sufficiently air-evacuated to provide at least a partial vacuum in said blood collection chamber.

* * * * *